US008715396B1

(12) United States Patent
Kippeny et al.

(10) Patent No.: US 8,715,396 B1
(45) Date of Patent: May 6, 2014

(54) SURFACE MODIFICATION OF SUPERADSORBENT MATERIAL FOR IMPROVED AIR SAMPLING APPLICATIONS AND METHODS OF MAKING SAME

(75) Inventors: Tadd C. Kippeny, Mount Airy, MD (US); Christopher S. Badorrek, Hagerstown, MD (US); Michael J. Bowers, II, Sykesville, MD (US); Christopher L. Rector, Lee's Summit, MO (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 0 days.

(21) Appl. No.: 13/593,758

(22) Filed: Aug. 24, 2012

Related U.S. Application Data

(63) Continuation-in-part of application No. 13/183,492, filed on Jul. 15, 2011.

(60) Provisional application No. 61/364,603, filed on Jul. 15, 2010, provisional application No. 61/527,162, filed on Aug. 25, 2011, provisional application No. 61/532,249, filed on Sep. 8, 2011, provisional application No. 61/532,257, filed on Sep. 8, 2011.

(51) Int. Cl.
*B01D 53/02* (2006.01)

(52) U.S. Cl.
USPC ................ 95/143; 502/11; 502/12; 502/177; 502/178; 502/179

(58) Field of Classification Search
USPC ......................... 502/11, 12, 177–179; 95/143
See application file for complete search history.

(56) References Cited

U.S. PATENT DOCUMENTS

| | | | | |
|---|---|---|---|---|
| 5,308,457 | A * | 5/1994 | Dalla Betta et al. | 95/143 |
| 2010/0107731 | A1* | 5/2010 | Kippeny | 73/23.41 |
| 2011/0147314 | A1* | 6/2011 | Kippeny et al. | 210/670 |

* cited by examiner

*Primary Examiner* — Christopher P Jones
(74) *Attorney, Agent, or Firm* — Daniel J. Long

(57) ABSTRACT

A method for providing superadsorption of polar organic compounds using a material system is provided. The method can comprise enhancing adsorption by means of using high surface area and mass transfer rates and decreased reactivity at surface sites attractive to the polar compounds; and employing consequence management by maintaining a high rate of adsorptivity combined with high fidelity and accuracy of the material system. A modified superadsorbent material for air sampling applications comprising a superadsorbent material treated with a solution, thereby forming a treated superadsorbent material, wherein the treated superadsorbent material is substantially hydrophobic and is capable of adsorbing polar compounds.

3 Claims, 5 Drawing Sheets

SURFACE MODIFICATION OF SUPERADSORBENT MATERIAL FOR IMPROVED AIR SAMPLING APPLICATIONS AND METHODS OF MAKING SAME

CROSS-REFERENCE TO RELATED APPLICATIONS

This application is a Continuation-in-Part of U.S. patent application Ser. No. 13/183,492 filed Jul. 15, 2011, now abandoned, and claims rights under 35 U.S.C. §119(e) from U.S. Patent Application Ser. No. 61/364,603 filed Jul. 15, 2010 and claims priority from U.S. Ser. Nos. 61/527,162 filed Aug. 25, 2011, 61/532,249 filed Sep. 8, 2011 and 61/532,257 filed Sep. 8, 2011, the contents of which are incorporated herein by reference.

STATEMENT OF GOVERNMENT INTEREST

This invention was made with United States Government Support under Contract No. HR0011-08-C-0056 awarded by DARPA. The United States Government has certain rights in this application.

BACKGROUND OF THE INVENTION

1. Field of the Invention

The present invention relates to providing enhanced adsorption and more particularly to methods for providing enhanced adsorption via high surface area and mass transfer rates.

2. Brief Description of Related Art

Current superadsorbent materials do not provide adequate adsorption of polar compounds, including alcohols, amines, and hydrocarbons containing carboxyl groups. Each of these groups represents a portion of chemicals listed as chemical warfare agents, toxic industrial compounds, toxic industrial materials, and other harmful volatile organic compounds.

The combined act of sampling the air in an environment and subsequently detecting the adsorbed samples is defined as consequence management. The current methods of performing this function do not have any solution that can adsorb a wide variety of polar compounds and/or volatile organic compounds and rapidly desorb those compounds with fidelity and accuracy.

A need exists, therefore, for an improved method for providing enhanced adsorption during air sampling.

SUMMARY OF THE INVENTION

The present invention is a method for providing superadsorption of polar organic compounds using a material system comprising the steps of: enhancing adsorption by means of using high surface area and mass transfer rates and decreased reactivity at surface sites attractive to the polar compounds; and employing consequence management by maintaining a high rate of adsorptivity combined with high fidelity and accuracy of the material system.

According to the present invention, the surface modifications of the superadsorbent material lead to enhanced performance in adsorption of the classes of compounds listed above, which in turn allows for 1) the identification of the compounds in the original air sample, and 2) the ability to correlate a relative concentration of the analytes to an original concentration. While the surface modification of the material allows for more polar compounds to be adsorbed, the desirable physical properties such as very high surface area and mass transfer rates of the superadsorbent material are retained. Additionally, the superadsorbent material is not affected by humidity. The nanoporous carbon found in the superadsorbent material has been demonstrated to operate over 80% relative humidity environment with minimal change in performance due to water adsorption. Treated nanoporous carbons can maintain greater than 50% of total pore volume even at 80% relative humidity.

The combined act of sampling the air in an environment and subsequently detecting the adsorbed samples is defined as consequence management. The current methods of performing this function do not have any solution that can adsorb a wide variety of volatile organic compounds and rapidly desorb it with very high fidelity and accuracy. The present invention is very hydrophobic while still having the capability to capture polar compounds and desorb the chemicals to provide analysis of an environmental exposure event.

Those skilled in the art will appreciate that the high rate of adsorptivity combined with high fidelity and accuracy of the material system of the method of this invention provides a solution for improved consequence management.

BRIEF DESCRIPTION OF THE DRAWINGS

The present invention is further described with reference to the following drawings wherein:

FIG. 1 is a graph showing the desorption results of an analyte mix of polar compounds from the unmodified sorbent and the sorbent modified with alkene thermo-grafting;

FIG. 2 is a graph showing the desorption results of an analyte mix of alcohols from the unmodified sorbent and the sorbent modified with fluorobenzene coupling;

FIG. 3 is a graph showing the desorption results of an analyte mix containing electron donating compounds from the unmodified sorbent and the sorbent modified with a high oxidation treatment;

FIG. 4 is a graph showing the desorption results of an analyte mix containing halocarbons from the unmodified sorbent and the sorbent modified with a low oxidation treatment; and FIG. 5 is a graph showing the desorption results of an analyte mix containing electron donating compounds from the unmodified sorbent and the sorbent modified with a low oxidation treatment.

DETAILED DESCRIPTION OF THE PREFERRED EMBODIMENTS

The present invention of modifying the surface chemistry of a superadsorbent material offers a way to provide enhanced adsorption via high surface area and mass transfer rates, and decreased reactivity at surface sites attractive to polar compounds. Taken together, these characteristics lead to less material incorporated into an environmental sampling device or chemical trapping system while increasing the fidelity and accuracy for identification of compounds in initial air samples.

In a preferred embodiment of the present invention, a carbide-derived nanoporous carbon is used as a superadsorbent material. The observed pore sizes and porosity can be tuned by altering the processing parameters to give broad or narrow atomic, molecular, or gas sorption selectivity. Many such carbides exist and can be partially demetalized to leave residual metal content, with associated catalytic activity, providing a facile fabrication route to a sorption substrate with uniform physical characteristics but diverse analyte capture and decontamination properties. Exemplary carbides include Mo$_2$C, TiC, SiC, ZrC, WC, W$_2$C, VC, and Cr$_3$C$_2$. Other rare and metastable carbides include CuC$_2$, ZnC$_2$, Ni$_3$C, Co$_3$C, Fe$_3$C, NbC, HfC, and TaC.

Additionally, nanoporous carbons are very hydrophobic. This water-repelling characteristic is extremely important to sorption properties as the pores of many sorbent materials fill rapidly with droplets from water vapor in humid environments, dramatically reducing performance. By chemically modifying the surface chemistry, treated nanoporous carbons can maintain greater than 50% of total pore volume even at 80% relative humidity.

The present invention is further defined by the following working examples:

Example 1

Figure 1:
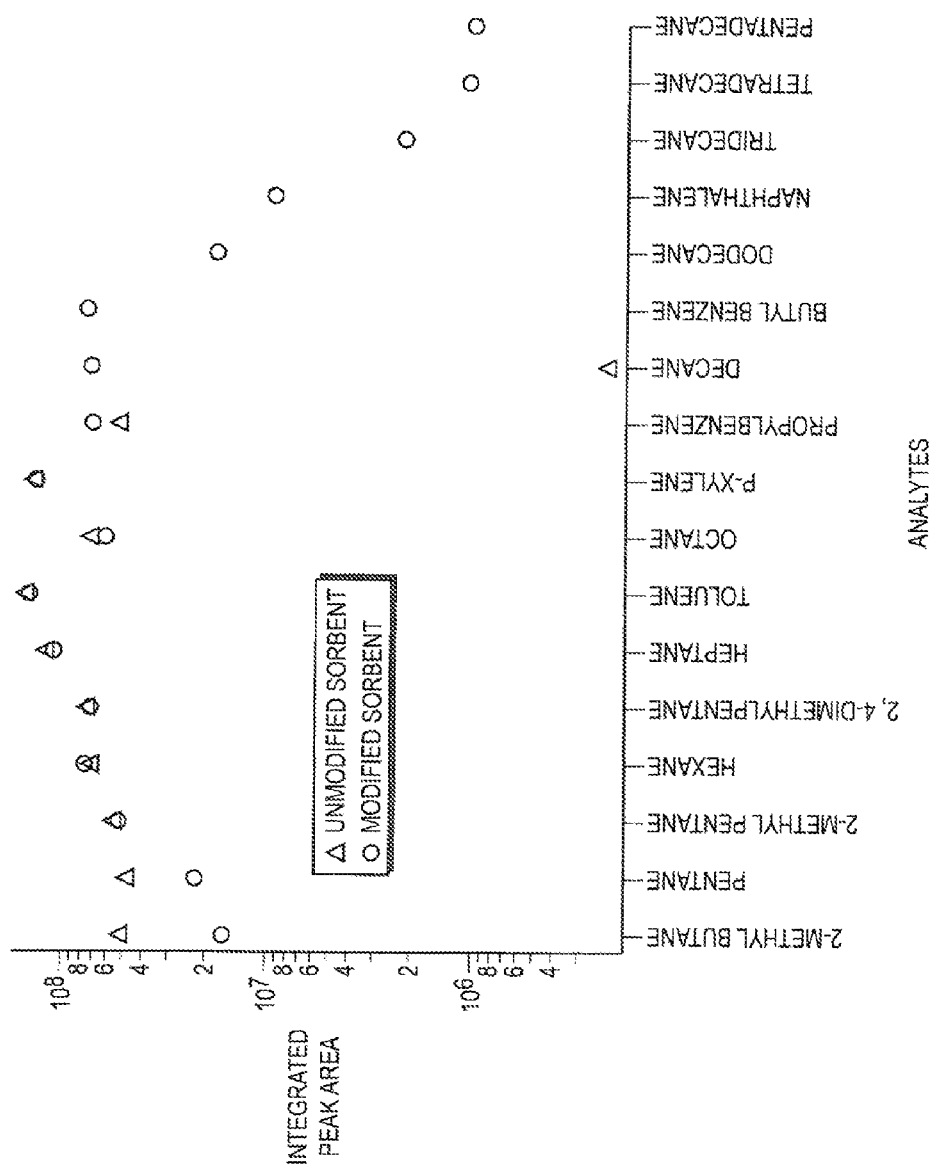

Referring to FIG. 1, a surface modification involving alkene thermo-grafting was performed on a superadsorbent material, for example, a carbide-derived carbon (CDC). The surface modification was performed by using a Schlenk flask charged with 8-10 mL of an alkene and was degassed by evacuation and flushed with nitrogen three times. In a preferred embodiment of the invention, the alkene is either methyl 10-undecenoate or 1-decene. Then, 500 mg of the CDC was added and the mixture was heated to 165-170° C. under a nitrogen atmosphere overnight. After allowing the reaction mixture to cool, the CDC was filtered off and washed with 50 mL dichloromethane and 50 mL of methane. Each sample was then subjected to Soxhlet extraction with dichloromethane overnight and dried under a vacuum for several hours.

The results in FIG. 1 show the desorption results of an analyte mix with polar compounds from the unmodified sorbent and the sorbent modified using alkene thermo-grafting. The experiment included desorbing for 2 minutes at 250° C. and at 350° C. for the following 3 minutes except for the baseline experiment. Clearly, the modification increases the adsorbent's ability to desorb polar compounds. The alkene-treated CDC desorbed every hydrocarbon in the mixture, including C12-C15 chains.

Example 2

Figure 2:
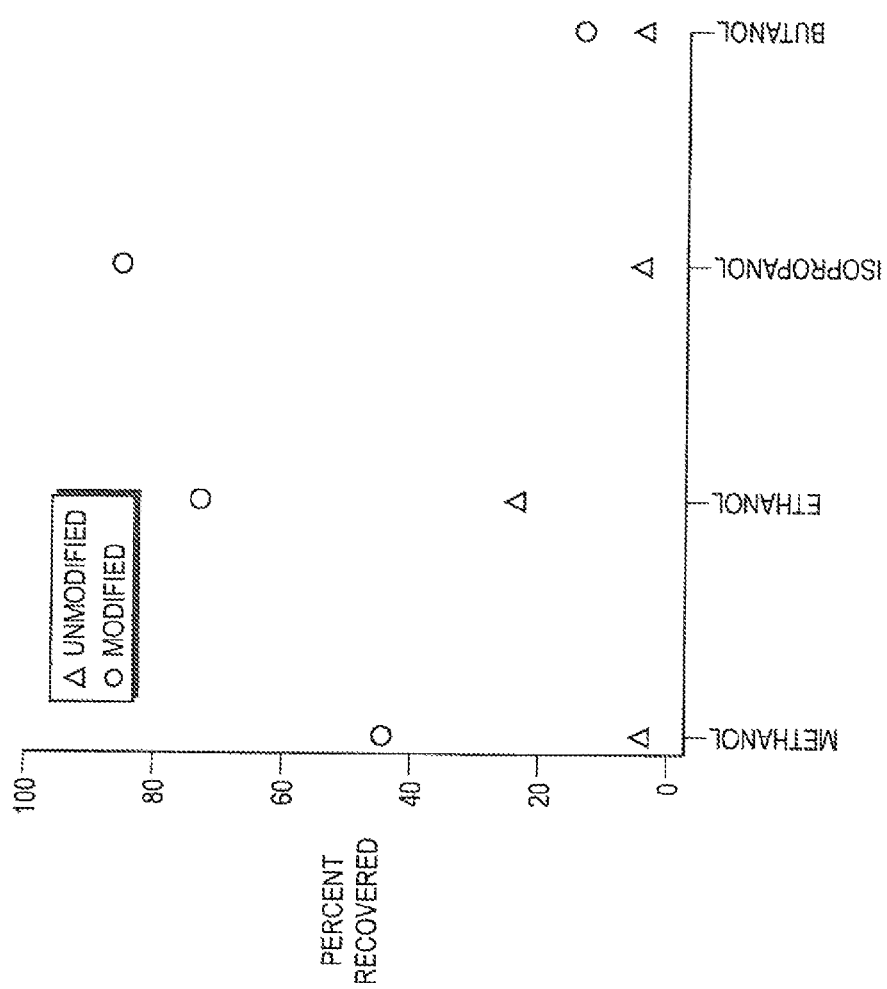

Referring to FIG. 2, a surface modification involving a fluorination treatment was performed on a superadsorbent material, for example, a CDC. The surface modification was performed by coupling 4-fluoro-aniline to the carbon substrate through the use of a diazonium salt intermediate. Specifically, this process required an initial amount of 1.0 mL solution of 4-fluoro-aniline in 15 mL tetrahydrofuran (THF). Each graphite sample was placed in a glass container with a magnetic stir bar at its bottom. Care was taken to position the graphite substrates by means of the Teflon strand just above the stir bar. In order to allow for eventual nitrogen evolution, N$_2$ gas being released from the reaction upon the decomposition of the diazonium salt, an empty gas balloon was inserted into the septa. Initially, 10 mL of isopentyl nitrite (IPN) was added. It was found that the use of three 5 mL aliquots of IPN, introduced in the glass container over a 15 hour time period (every 5 hours), has proven more efficient than supplying the entire amount of reagent from the very beginning. As revealed by the recorded larger electrochemical signal, sequential addition of IPN yields a more advanced surface modification than one-time addition. This electrochemical signal is proportional to the surface coverage of tether, being a result of a more profound surface modification.

Results in FIG. 2 show the desorption results of an analyte mix of alcohols with increasing numbers of carbons, ranging from one carbon to four carbons, from the unmodified sorbent and the sorbent modified using fluorobenzene coupling to decrease adsorption binding energies. Clearly, the modification increases the adsorbent's ability to desorb polar alcohols. In the unmodified case, the largest desorption yield is about 25% analyte recovery for ethanol and in all other cases, desorption was minimal. The modified sorbent yields desorption as high as 85% recovery such as in the case of isopropanol.

Example 3

Figure 3:
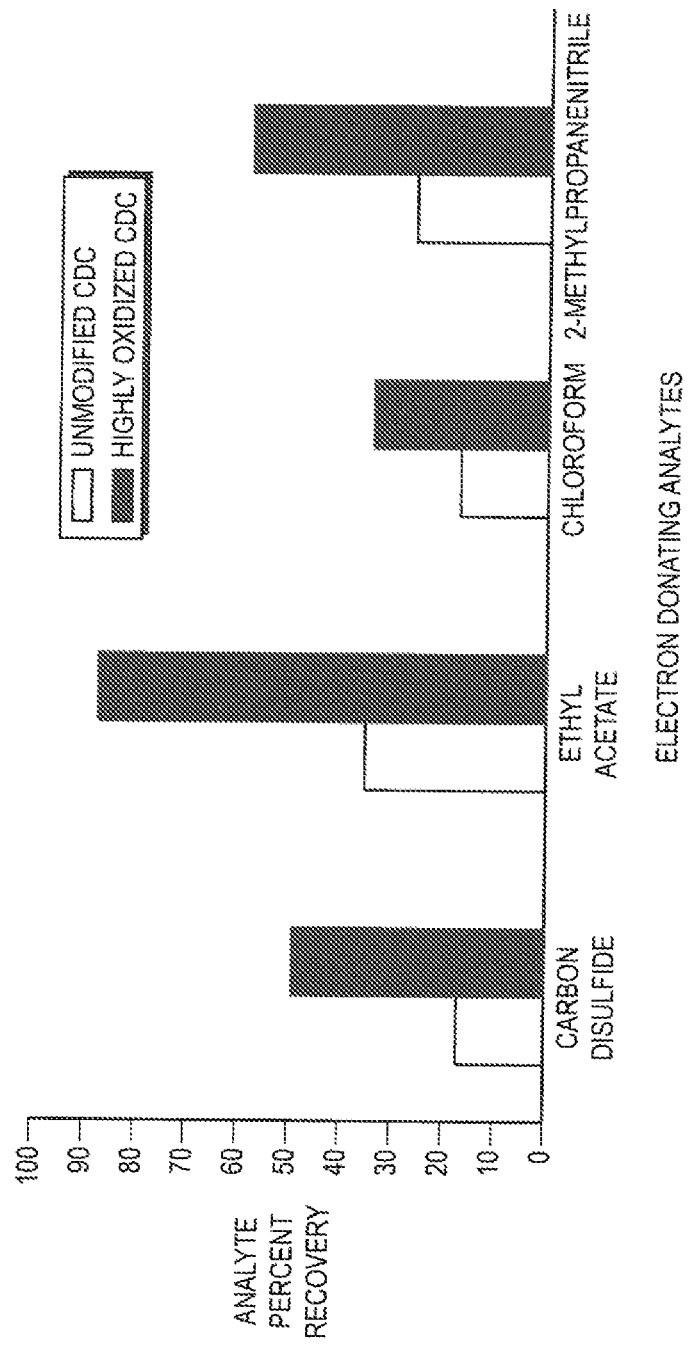

Referring to FIG. 3, a surface modification involving a high oxidation treatment was performed on a superadsorbent material, for example, a CDC. The surface modification was performed by treating the superadsorbent material with a 1:1 ratio mixture of concentrated sulfuric acid and nitric acid (H$_2$SO$_4$:HNO$_3$). Specifically, the gas phase functionalization for the highly oxidized surface was completed by placing the unmodified sorbent in concentrated H$_2$SO$_4$:HNO$_3$ using an argon bubbler and a 1:1 ratio at room temperature. The oxidized sorbent is washed to pH neutral and stored under about 1×10$^{-2}$ Torr at 120° C. overnight.

Results in FIG. 3 show the desorption results of an analyte mix containing different electron donating compounds, such as carbon disulfide, ethyl acetate, chloroform, and 2-methylpropanenitrile, from the unmodified sorbent and the sorbent modified with the high oxidation surface treatment. Clearly, the oxidation of the surface increases the adsorbent's ability to desorb all four examples of electron donating compounds. This is likely due to the oxidation treatment reacting at step edges that are reactive toward electron donors. The increase in percent recovery ranges from about 15% to about 50% from the unmodified desorption results.

Example 4

Figure 4:
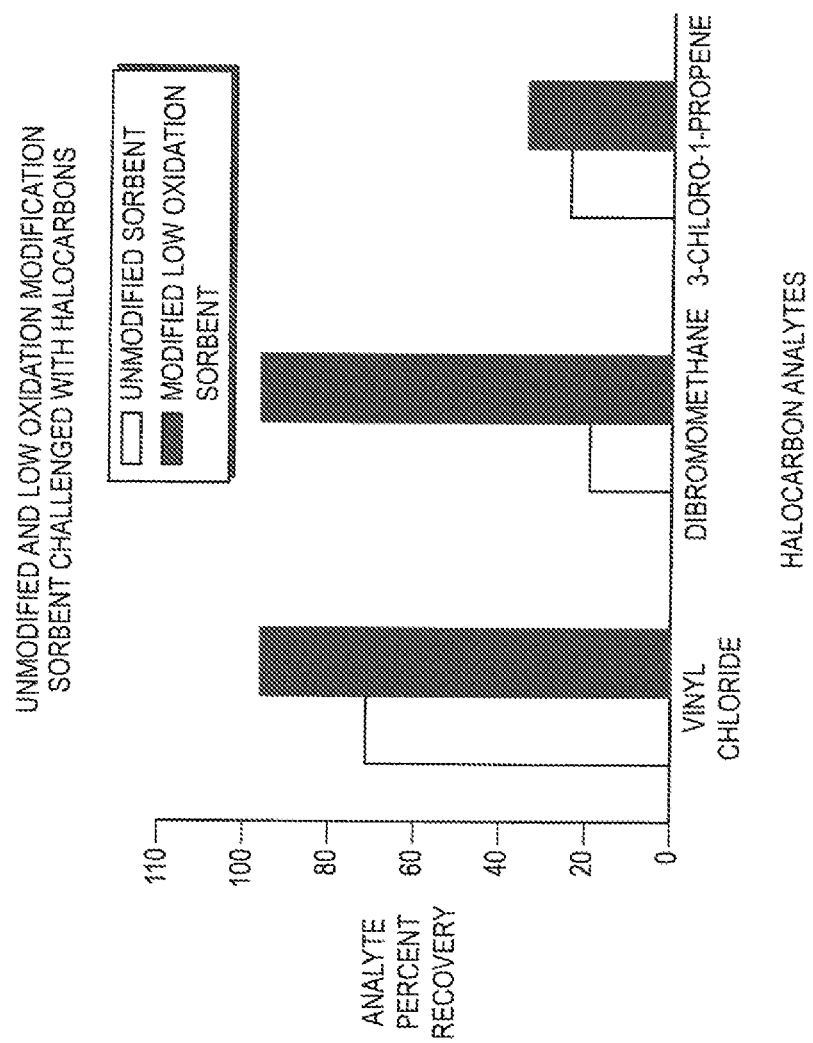
Figure 5:
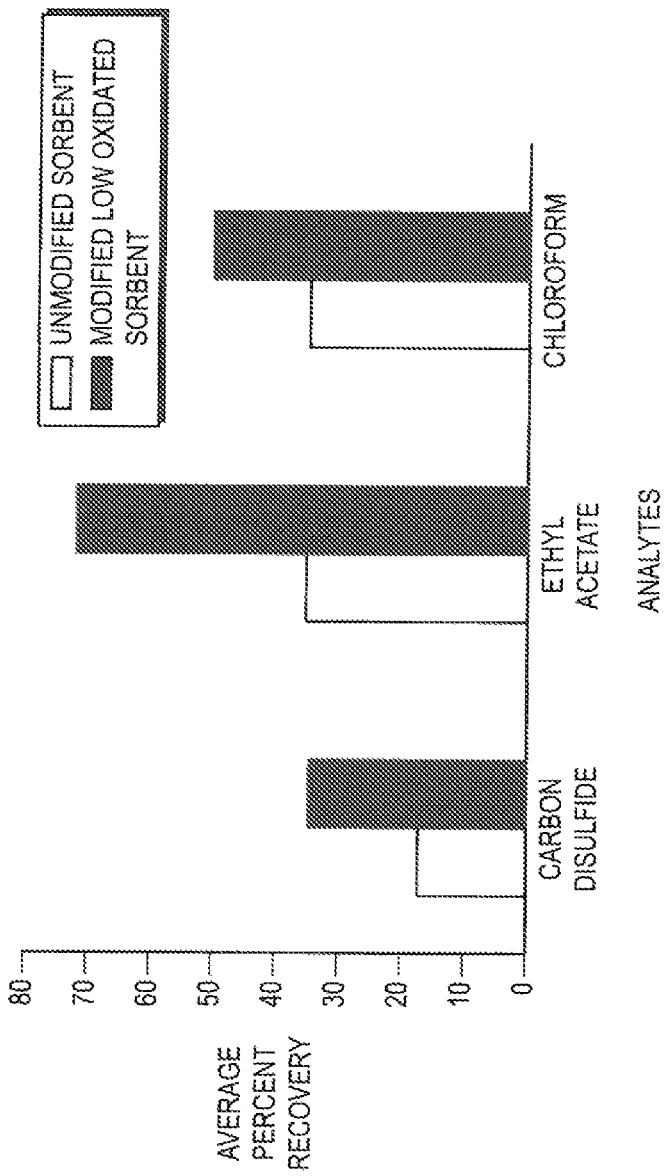

Referring to FIGS. 4 and 5, a surface modification involving a low oxidation treatment was performed on a superadsorbent material, for example, a CDC. The surface modification was performed by treating the superadsorbent material with pure carbon monoxide. Specifically, 600 mg of CDC was placed in two fast flow desorption tubes in a gas flow line that was placed between two infrared lamps. Pure carbon monoxide was flowed through the tubes at 20 mL/min for 1 hour. In the process, the power on the infrared was adjusted to 60% such that the lamps heated the CDC to 325° C. After 1 hour, the lamps were turned off and carbon monoxide was continually slowed during a 20 minute cool down period. The material was conditioned using the traditional technique at 325° C. under helium for 90 minutes.

Results in FIG. 4 show the desorption results of an analyte mix containing different halocarbons, such as vinyl chloride, dibromomethane, and 3-chloro-1-propene, from the unmodified sorbent and the sorbent modified with the low oxidation treatment. Clearly, the oxidation of the surface increases the adsorbent's ability to desorb all three examples of halocarbons. In the modified case, the increase in percent recovery ranges from about 15% to about 80% from the unmodified desorption results. Additionally, results in FIG. 5 show the desorption results of an analyte mix containing different electron donating compounds, such as carbon disulfide, ethyl acetate, and chloroform, from the unmodified sorbent and the sorbent modified with the low oxidation treatment. The oxidation of the surface again increased the adsorbent's ability to desorb all three examples of electron donating compounds.

The increase in percent recovery ranges from about 15% to about 35% from the unmodified desorption results.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A method for air sampling comprising the steps of:
   providing a modified superadsorbent material treated with a solution, thereby forming a treated superadsorbent material, the treatment including modifying the material covalently with 4-fluoro-aniline, the treated superadsorbent material being substantially hydrophobic and capable of adsorbing polar compounds,
   performing the air sampling such that analytes adsorb to the surface of the modified superadsorbent material.

2. The method of claim 1, wherein the superadsorbent material is a carbide-derived carbon.

3. A method for air sampling comprising the steps of:
   providing a modified superadsorbent material including a carbide-derived carbon having a surface chemically modified by coupling 4-fluoro-aniline to the surface, wherein the chemically modified surface is substantially hydrophobic and capable of adsorbing polar compounds,
   performing the air sampling such that analytes adsorb to the surface of the modified superadsorbent material.

* * * * *